United States Patent [19]
Prudom

[11] 3,979,283
[45] Sept. 7, 1976

[54] MICROBIAL DEGRADATION OF DDT
[75] Inventor: Carolina M. Prudom, McLean, Va.
[73] Assignee: Bioteknika International, Inc., Springfield, Va.
[22] Filed: Sept. 25, 1974
[21] Appl. No.: 509,115

[52] U.S. Cl. .................................. 210/11; 195/2
[51] Int. Cl.² .......................................... C02C 5/10
[58] Field of Search ............. 210/11, 2; 195/2, 3 R, 195/3 H

[56] References Cited
UNITED STATES PATENTS

| | | | |
|---|---|---|---|
| 3,660,278 | 5/1972 | Mimura et al. | 210/11 |
| 3,769,164 | 10/1973 | Azarowicz | 195/2 |
| 3,779,866 | 12/1973 | Azarowicz | 195/2 |
| 3,899,376 | 8/1975 | Azarowicz | 210/11 |

Primary Examiner—Thomas G. Wyse
Attorney, Agent, or Firm—Stewart and Kolasch, Ltd.

[57] ABSTRACT

A process for the microbial degradation of DDT which comprises treating the DDT with certain non-pathogenic, hydrocarbon-utilizing strains of Nocardia, Candida and penicillium until the DDT has been substantially degraded. The process is effective for degrading DDT as it may be present as a pollutant or contaminant in water, in industrial effluents, in various land areas such as industrial sites and the like or in varied laboratory or commercial installations. The process may also be used to clean up and degrade mixtures of DDT and various hydrocarbon oils or petrochemicals wherever their presence constitutes a deleterious pollutant.

9 Claims, No Drawings

MICROBIAL DEGRADATION OF DDT

BACKGROUND OF THE INVENTION

This invention relates to a process for the microbial degradation of dichloro-diphenyl-trichloroethane (hereinafter referred to as DDT). More particularly, it relates to a method for degrading DDT by means of microorganisms in order to clean up and eliminate this pollutant as it may occur in the open sea, inland fresh waters, tidal pools, harbors and the like, industrial effluent discharges, sewage and other pipeline systems, farm soil or other land areas including industrial sites, etc. The invention is applicable not only for cleaning up DDT as a contaminant or pollutant in open environmental systems, but also in closed systems as, for example, in industrial, commercial or government plants and installations and in various laboratory operations.

Environmental cleanup is of much concern to the country and to the world today. DDT is a chemical that was widely used as an effective insecticide and pesticide; however, its use has been banned in many jurisdictions because of its potential hazard to human health. Hence, it would be extremely desirable to be able to use this substance safely and effectively without the danger of contamination. The present invention makes it possible to degrade DDT microbially so that its use is again made possible.

DDT is a very persistent substance and is extremely difficult to degrade once it is present in the environment. Residues of DDT have been noted in fish, birds and mammals, which include those used for human food as well as the wild animals. Although the data are incomplete at the present time, there is significant evidence that most humans have some residues of DDT in their tissues. The effect on humans of such residues is also unclear at the present time, but some evidence indicates very severe and harmful effects from DDT poisoning. As with many other chlorinated hydrocarbons, such as PCBs, even small dosages of DDT can be toxic. In any event, the presence of DDT in the environment has been a great concern to scientists and other people concerned with health, safety and welfare, and there has been a great need for the development of a procedure for the degradation of such substances.

Accordingly, one of the objects of the present invention is to provide a method for degrading DDT wherever it may appear as a contaminant or pollutant.

Another object of the present invention is to provide a process for the microbial degradation of DDT wherever desired; for example, as a means of cleaning up closed and open waters, industrial effluent discharges, polluted marshlands estuaries, marine environments, disposal lagoons, contaminated industrial areas, soils and farmlands, and in other situations where DDT may become accumulated.

A further object of the invention is to provide a procedure for degrading DDT readily, efficiently, and relatively economically.

A still further object of the invention is to provide microorganisms that are capable of degrading DDT, leaving a detoxified and beneficial cell mass, these microorganisms being completely nonpathogenic to marine fauna and flora, humans and animals.

Yet another object of the invention is to provide a method for the degradation of DDT wherein there is no need for the handling, transporting and storage of heavy, bulky equipment.

These and other objects and advantages of the present invention will become apparent to those skilled in the art from a consideration of the following specification and claims.

SUMMARY OF THE INVENTION

In accordance with the present invention, the above objectives are attained and an advantageous procedure for the microbial degradation of DDT has been discovered employing particular strains of microorganisms. The distinct, unique advantage of the present invention is that all of the materials used are derived originally from edible substances which are not toxic. It is applicable equally to the degradation of industrial wastes in general as well as to the degradation of DDT in open and closed aqueous systems no matter how the system was contaminated and polluted. In the present invention, advantage has been taken of judiciously choosing microorganisms which are capable of degrading DDT and using them as a carbon source for growth.

The present invention comprises a purely biological process in which certain selected microorganisms break down the DDT and converts it into a mass of edible, nontoxic cells; i.e., a protein mass. In an outdoor application, this cell mass can be channeled into the food chain to feed higher forms of life and, thus, a very advantageous end result is achieved in addition to solving the problem of DDT contamination. There is no need for ancillary cleanup operations when DDT is degraded in accordance with the invention and, as pointed out above, there is also no need for the handling, transporting and storing of heavy, bulky equipment.

The microorganisms employed in the present invention belong to the genera Nocardia, Candida and Penicillium. The following specific microorganisms all completely novel and unobvious, are utilized in the present invention. These microorganisms are special species which have been adapted to achieve the objectives of the invention. They have been deposited with the American Type Culture Collection in Rockville, Maryland, and have been given the designated ATCC catalogue numbers:

Candida lipolytica (BI 2002) ATCC 20255
Nocardia globerula (BI 1039) ATCC 21505
Nocardia rubra (BI 1002) ATCC 21508
Penicillium sp. (BI 3005) ATCC 20369

The characteristics and properties of these microorganisms are described in U.S. Pat. No. 3,769,164, issued on Oct. 30, 1973, to the assignee of the present application and in copending application Ser. No. 334,986, filed on Feb. 23, 1973, now U.S. Pat. No. 3,899,376.

Various media can be employed in handling these cultures. All of the microorganisms employed in the present invention will grow on media with 100% marine water, with part marine water and part tap water, or in distilled water. The following medium has been found to be quite satisfactory as a general use, all-purpose medium for maintaining stock cultures:

All-Purpose Medium

| | |
|---|---|
| Heart infusion broth (Difco) | 23.0 g. |
| Yeast extract (Difco) | 3.0 g. |
| Glycerol | 5.0 ml. |
| Glucose | 5.0 g. |
| Agar | 15.0 g. |

-continued

| | |
|---|---|
| Water | 1000.0 ml. |

The standard Bushnell-Haas broth has been found to be quite suitable as a growth medium on the laboratory scale. A typical medium comprises the following ingredients:

| | |
|---|---|
| Yeast-nitrogen base (Difco) | 1.0 g. |
| Yeast extract (Difco) | 1.0 g. |
| $MgSO_4$ | 0.2 g. |
| $CaCl_2$ | 0.02 g. |
| $KH_2PO_4$, Monobasic | 1.0 g. |
| $K_2HPO_4$, Dibasic | 1.0 g. |
| $NH_4NO_3$ | 1.0 g. |
| $FeCl_3$ | 0.05 g. |
| Bromthymol blue | 0.08 g. |
| Water | 1000.0 ml. |

The following medium has been found to be particularly advantageous for the large-scale production of the desired cultures:

| | |
|---|---|
| Skim milk (0.4%) | 2.0 lbs. |
| Cottonseed meal (1.8%) | 9.0 lbs. |
| Marine salts (0.02%) | 0.1 lb. |
| $(NH_4)_2HPO_4$, Dibasic (0.1%) | 0.5 lb. |
| Hydrocarbon (0.44%) | 2.2 lbs. |
| Tap water | 60.0 gal. |

Instead of the marine salts and tap water, native sea water can be used in the above medium. Aeration is usually provided to supply oxygen to the fermenter vessel or tank. Generally, the microorganism cells are harvested after about three or four days of cultivation. A large batch vessel or fermenter seeded with a young culture equivalent to about 2% or more of the total capacity of the fermenter is used for producing large quantities of the cultures. If necessary, an antifoam agent can be employed therein; for example, Dow Antifoam A, or crude oil.

Hence, either a synthetic culture medium or a natural nutrient medium is suitable for the growth of the microorganism strains employed in the present invention as long as it contains the essential nutrients for the growth of the particular microorganism strain or strains used. Such nutrients are well known in the art and include substances such as a carbon source, a nitrogen source, inorganic compounds and the like which are utilized by the microorganisms employed in appropriate amounts.

The microorganisms used in the present invention grow and survive in an aqueous nutrient medium containing a hydrocarbon or a mixture of hydrocarbons as the main carbon source. Such hydrocarbons include straight- and branched-chain paraffins (alkanes) ranging from gaseous alkanes, such as methane and propane, liquid or semi-solid alkanes, such as n-pentane, n-octane, n-decane, n-dodecane, n-hexadecane, isopentane, isooctane, and including long-chain solid paraffins having high melting points, cycloparaffins such as cyclohexane and cyclooctane, straight- and branched-chain olefins such as pentene-2, hexene-1, octene-1, octene-2, etc., cycloolefins such as cyclohexene, aromatic hydrocarbons such as benzene, o-xylene, naphthalene, phenanthrenes, anthracenes, etc., and mixtures thereof, as well as mixed hydrocarbons such as kerosene, light oils, heavy oils, paraffin oils, petroleum crudes, jet fuels, gasoline, etc. Other organic substances, such as alcohols, aldehydes, ketones, organic acids, phenolics and aromatic heterocyclic and carbocyclic compounds, are utilized by the microorganisms described in the present application.

Small amounts of other carbon sources such as carbohydrates, for example, glucose, fructose, maltose, sucrose, starch, starch hydrolysate, molasses, etc., or any other suitable carbon source such as glycerol, mannitol, sorbitol, organic acids, etc., may be used in the culture medium along with the hydrocarbons. These substances may be used either singly or in mixtures of two or more.

As a nitrogen source, various kinds of inorganic or organic salts or compounds, such as urea or ammonium salts such as ammonium chloride, ammonium sulfate, ammonium nitrate, ammonium phosphate, etc., or one or more than one amino acid or crude protein mixed in combination, or natural substances containing nitrogen, such as cornsteep liquor, yeast extract, meat extract, fish meal, peptone, bouillon, casein hydrolysates, fish solubles, rice bran extract, etc., may be employed. These substances may also be used either singly or in combinations of two or more.

Inorganic compounds which may be added to the culture medium include magnesium sulfate, sodium phosphate, potassium dihydrogen phosphate, potassium monohydrogen phosphate, iron sulfate or other iron salts such as ferric trichloride, manganese chloride, calcium chloride, sodium chloride, ammonium nitrate, etc.

The microorganisms employed in the present invention are cultured under aerobic conditions, such as aerobic shaking of the culture or with stirring and aeration of a submerged culture, at a temperature of, for example, about 5° to 35°C., preferably 28°–30°C., and at a pH of, for example, about 5 to 8, preferably 7–7.6. The microorganisms are harvested at an appropriate time and are used as discussed below.

DETAILED DESCRIPTION OF THE PREFERRED EMBODIMENTS

The process of the invention can be used to remove DDT from locations wherever its presence constitutes a deleterious pollution. Thus, with this process, it becomes possible to clean up and degrade DDT on the open sea, in harbors, rivers and other inland waters, on various kinds of beaches and soils, in industrial effluent systems, in sewage disposal systems, in various laboratory systems, etc.

EXAMPLE 1

Into each of four Erlenmeyer flasks there was added 99 ml. of the standard Bushnell-Haas medium described above and 1 ml. of a dirty effluent material containing DDT. Then, 1 ml. of a slurry of each of the following microorganisms was inoculated into each flask, and the flasks were shaken at 250 r.p.m. at room temperature (28°C.) for two days. At the end of two days (48 hours), visual examination of the flasks showed the following results:

| Flask | Culture | |
|---|---|---|
| 1. | Nocardia rubra (BI 1002) ATCC 21508 | Heavy cell growth |
| 2. | Nocardia sp. (BI 1008) | Heavy cell growth |
| 3. | Nocardia globerula (BI 1039) | Moderate cell |

-continued

| Flask | Culture | |
|---|---|---|
| 4. | ATCC 21505 Candida lipolytica (BI 2002) ATCC 20255 | growth Moderate cell growth |

A fifth flask, used as a control and containing 99 ml. of the Bushnell-Haas medium and 1 ml. of the same DDT-containing effluent, remained medium clear in appearance during the aerobic shaking of the flask for two days.

The contents of the flasks were autoclaved after shaking had been continued for an additional eight days and analyzed by means of gas-liquid chromatography with the following results:

| Flask | Culture | DDT left (mg/100 ml.) |
|---|---|---|
| Control | None | 36.23 |
| No. 1 | Nocardia rubra | 12.04 |
| No. 2 | Nocardia sp. | 22.61 |
| No. 3 | Nocardia globerula | 21.66 |
| No. 4 | Candida lipolytica | 30.07 |

The above results show that from about 67% (Flask No. 1) to about 16% (Flask No. 4) by weight of the DDT originally present in the dirty effluent material was degraded by the microorganisms employed.

Additional testing with these microorganisms indicated that degradation is basically achieved after two to four days of aerobic shaking and then levels off, so that two to four days of microbial action is considered to be the optimum time necessary to obtain the desired degradation of the DDT.

EXAMPLE 2

One gram of pure DDT was dissolved in 300 ml. of hexane, providing a solution containing 3,330 p.p.m. of DDT. One ml. of said DDT stock solution was added to each of several 250-ml. Erlenmeyer flasks containing 99 ml. of standard Bushnell-Haas medium. The following microorganisms were inoculated into the flasks and aerobic shaking of the flasks was conducted at 28°C. for four days with the following results:

| Flask | | Assay |
|---|---|---|
| 1. | Nocardia rubra (BI 1002) ATCC 21508 | 416 × $10^4$ Cells/ml. |
| 2. | Nocardia sp. (BI 1008) | 127 × $10^4$ cells/ml. |
| 3. | Nocardia globerula (BI 1039) ATCC 21505 | 102 × $10^4$ cells/ml. |
| 4. | Candida lipolytica (BI 2002) ATCC 20255 | 23 × $10^4$ cells/ml. |

The cell growth as measured by plating out and assay is a measure of the ability of the microorganisms to grow and thereby degrade the carbon-source substances, i.e., the DDT herein.

EXAMPLE 3

Using the same procedure as described in Example 2, Penicillium sp. (BI 3005) ATCC 20369 is inoculated into a flask containing 99 ml. of standard Bushnell-Haas medium and 1 ml. of said DDT-containing effluent material. After aerobically shaking the flask for three days, the cell growth is heavy and the liquid becomes clear, indicating that a substantial degradation of the DDT by microbial action has taken place.

Substantially the same results could be obtained by using a mixture of two or more of said microorganisms. Hence, the described microorganisms may be used either singly or in various combinations of two or more to degrade DDT in accordance with the objectives of the invention.

Generally, the degradation of DDT on a large scale is conducted in a multi-tank installation. Less often, degradation is done in outdoor environments. In open-water applications, it is quite feasible to seed or disperse the microorganisms employed by means of boats, aircraft or other vehicles as appropriate. Even though DDT is heavier than water, degradation takes place since the microorganisms become dispersed downward with time to the benthic mud. The mixture employed preferably includes a cellulose absorbent such as, for example, straw, bagasse, pine bark mulch, sawdust or other forest or agricultural products. Additive nutrients for the microorganisms are also mixed with the absorbent, such as cottonseed protein or other inexpensive agricultural by-products and inorganic salts of nitrogen and phosphorus. The process is applicable from just above freezing temperature (about 4°C.) to about 39°C. The degradation of the DDT will begin upon spreading the mixture on the surface of the water. Complete degradation may take place as early as two days to one week, but could take longer depending upon the DDT concentration and the temperature conditions. Of course, it is not necessary to use an absorbent, and the microorganisms can be used as a foam or in a slurry, powdered or pelletized form with added nutrients.

With an application on dry or damp soil, the mixture of microorganisms and nutrients can be applied to the soil and the mixture will work aerobically and anaerobically to degrade the contaminant DDT. This procedure is especially effective on extremely wet surfaces such as marsh lands, farm lands or industrial land sites such as trucking areas and railroad sidings.

The most practical application of the present invention involves the degradation of DDT in waste materials in a pollution control system. In this case, the effluent material to be degraded can be placed into large holding tanks, for example, and the mixture of microorganisms and nutrients added thereto, whereby degradation will take place as described above. Stirring and aeration of the mixture inside the tank is advantageously employed to provide a more rapid degradation. A single tank system may be used, or a multi-tank system may be employed wherein the effluent material is moved from tank to tank at specified times. Additional microorganism cultures and nutrients for the microorganisms may be added to the subsequent tanks as desired, for example, to obtain a desired or necessary level of DDT concentration. The degraded effluent, for example, may then be discharged into a lake, stream, marsh, etc., or the water may be recirculated within the industrial plant.

Since the microorganisms of the present invention are also capable of degrading petroleum and various petrochemical substances, as described in U.S. Pat. No. 3,769,164, the process of the present invention may be employed with effluents which contain petroleum or petrochemical contaminants as well as DDT, for example, emulsified cutting oils or rolling mill coolants. The degradation of one substance is not affected by the degradation of other substances, and a complete cleanup operation, for example, a total industrial waste problem, can be effectuated in this manner.

The microorganism or mixture of microorganisms is advantageously added in slurry form in an amount of about 1 to 5%, preferably 2%, by volume to an aqueous solution containing about 10 p.p.m. to about 15% by weight of DDT for optimum degradation action. If the mixture to be degraded contains oil and other organic pollutants besides DDT, a concentration of several percent (W/V) of microorganism-nutrient mixture is usually sufficient to be effective. About 1 to 5% by weight is desirable.

It is to be noted that a balanced nutritional medium, including a carbon source and additive nitrogen and phosphorus nutrients, is provided for the microorganisms employed. Since the additives used are of agricultural or forest sources, they are safe and nontoxic, since the microorganisms themselves are not toxic to humans, animals or fish. The carbon source can be the DDT alone, or a mixture of DDT and other hydrocarbons at concentrations of trace up to about 15% by weight.

It can thus be seen that the present invention provides a desirable and advantageous process for degrading and cleaning up the insecticide and pesticide, DDT, as well as petroleum or petrochemical pollutants and contaminants, by means of microbial degradation, so as to restore the polluted material to an ecologically-clean condition. This procedure is carried out safely and relatively economically without any harm whatsoever to human, animal or marine life.

It is to be understood that the present invention embraces the use not only of the above-described microorganisms, which are given merely for illustrative purposes, but it also includes the use of mutants produced from the specifically enumerated microorganisms, providing that they perform the same function. It is to be further understood that the invention includes the use of subcultures obtained from various standard microbiological techniques. Such mutants and/or subcultures may differ in certain respects from the above-described new strains, but they will work to degrade DDT in approximately the same manner as disclosed above.

The invention being thus described, it will be obvious that the same may be varied in many ways. Such variations are not to be regarded as a departure from the spirit and scope of the invention, and all such modifications as would be obvious to one skilled in the art are intended to be included herein.

I claim:

1. A process for the microbial degradation of dichlorodiphenyl-trichloroethane (DDT) which comprises treating the DDT with Penicillium sp. ATCC 20,369 for a sufficient time until the DDT has been substantially degraded.

2. The process of claim 1, wherein the microorganism is mixed with a cellulosic material.

3. The process of claim 1, wherein the microorganism is mixed with a cellulosic material, a nitrogen source and a phosphorus source.

4. The process of claim 1, wherein the microorganism is employed in a slurry form.

5. The process of claim 1, wherein the microorganism is employed in a pelletized form.

6. The process of claim 1, wherein the microorganism is employed in a powdered form.

7. The process of claim 1, wherein the microorganism is employed in the form of a foam.

8. The process of claim 1, wherein the DDT is contained in an aqueous solution and the microorganism is added thereto in slurry form in an amount of about 1 to 5% by volume.

9. The process of claim 1, wherein the DDT is contained in an aqueous solution which additionally contains hydrocarbon oils or other petrochemicals.

* * * * *